United States Patent
Zheng et al.

(10) Patent No.: US 11,511,277 B2
(45) Date of Patent: Nov. 29, 2022

(54) MICROFLUIDIC APPARATUS, AND SYSTEM AND METHOD FOR INTRODUCING SUBSTANCE INTO CELL

(71) Applicant: SHENZHEN INSTITUTES OF ADVANCED TECHNOLOGY, CHINESE ACADEMY OF SCIENCES, Shenzhen (CN)

(72) Inventors: Hairong Zheng, Shenzhen (CN); Wei Zhou, Shenzhen (CN); Long Meng, Shenzhen (CN); Lili Niu, Shenzhen (CN); Zhengrong Lin, Shenzhen (CN); Kaiyue Wang, Shenzhen (CN); Xiaowei Huang, Shenzhen (CN)

(73) Assignee: SHENZHEN INSTITUTES OF ADVANCED TECHNOLOGY, CHINESE ACADEMY OF SCIENCES, Shenzhen (CN)

( * ) Notice: Subject to any disclaimer, the term of this patent is extended or adjusted under 35 U.S.C. 154(b) by 688 days.

(21) Appl. No.: 16/606,355

(22) PCT Filed: Jan. 3, 2017

(86) PCT No.: PCT/CN2017/000080
§ 371 (c)(1),
(2) Date: Oct. 18, 2019

(87) PCT Pub. No.: WO2018/113034
PCT Pub. Date: Jun. 28, 2018

(65) Prior Publication Data
US 2020/0338548 A1  Oct. 29, 2020

(30) Foreign Application Priority Data
Dec. 23, 2016 (CN) .......................... 201611208089.6

(51) Int. Cl.
*B01L 3/00* (2006.01)
*C12N 15/89* (2006.01)

(52) U.S. Cl.
CPC ........... *B01L 3/50273* (2013.01); *B01L 3/508* (2013.01); *B01L 3/502715* (2013.01);
(Continued)

(58) Field of Classification Search
CPC ....... B01L 2200/0647; B01L 2300/123; B01L 2300/168; B01L 2400/0436;
(Continued)

(56) References Cited

U.S. PATENT DOCUMENTS

2011/0118139 A1* 5/2011 Mehta .................. B01L 3/5027
506/7
2014/0273229 A1 9/2014 Meacham et al.

FOREIGN PATENT DOCUMENTS

CN 103981090 A 8/2014
CN 104195028 A 12/2014
(Continued)

OTHER PUBLICATIONS

Translation of Chinese document CN 103981090 B (Year: 2016).*
(Continued)

*Primary Examiner* — Jennifer Wecker
*Assistant Examiner* — Jonathan Bortoli
(74) *Attorney, Agent, or Firm* — George McGuire

(57) ABSTRACT

Provided are a microfluidic apparatus, a method and system for introducing a substance into a cell. The microfluidic apparatus includes a cavity channel, a bulk wave generating device and a surface acoustic wave generating device; a microstructure is arranged on an inner wall of the cavity channel, and the microstructure is constructed for forming a bubble by a solution at the microstructure when the solution is injected into the cavity channel; the bulk wave generating
(Continued)

device is configured to generate a bulk wave, the bulk wave enables the bubble to resonate for generating a flow field; and the surface acoustic wave generating device is configured to generate a surface acoustic wave and control a position of at least one particle in the solution.

6 Claims, 4 Drawing Sheets

(52) U.S. Cl.
CPC ...... *B01L 3/502761* (2013.01); *C12N 15/895* (2013.01); *B01L 2200/0647* (2013.01); *B01L 2300/123* (2013.01); *B01L 2300/168* (2013.01); *B01L 2400/0436* (2013.01); *B01L 2400/0496* (2013.01)

(58) Field of Classification Search
CPC ....... B01L 2400/0496; B01L 3/502715; B01L 3/50273; B01L 3/502761; B01L 3/508; B01L 2400/0439; B01L 3/00; B01L 3/5027; C12N 15/87; C12N 15/895
See application file for complete search history.

(56) References Cited

FOREIGN PATENT DOCUMENTS

| CN | 104870077 A | | 8/2015 | |
|----|----|----|----|----|
| CN | 103981090 B | * | 5/2016 | ............ C12M 23/16 |

OTHER PUBLICATIONS

Fan et al "Spatiotemporally controlled single cell sonoporation" PNAS https://doi.org/10.1073/pnas.1208198109 (Year: 2012).*
International Search Report and Written Opinion Form PCT/ISA/210 and PCT/ISA237, International Application No. PCT/CN2017/000080, pp. 1-6, International Filing Date Jan. 3, 2017, dated Sep. 20, 2017.
Non-translated International Preliminary Report on Patentability, pp. 1-4, dated Jun. 25, 2019.

* cited by examiner

MICROFLUIDIC APPARATUS, AND SYSTEM AND METHOD FOR INTRODUCING SUBSTANCE INTO CELL

CROSS-REFERENCE TO RELATED APPLICATIONS

This is a National Stage Application, filed under 35 U.S.C. 371, of International Patent Application No. PCT/CN2017/000080, filed on Jan. 3, 2017, which claims priority to Chinese patent application No. 201611208089.6 filed on Dec. 23, 2016, contents of both of which are incorporated herein by reference in their entireties.

TECHNICAL FIELD

The disclosure relates to a technical field of biology and, in particular, to a microfluidic apparatus, and a system and method for introducing a substance into a cell.

BACKGROUND

The theory of gene therapy has been proposed and continuously lucubrated. A new development phase comes for the research of thoroughly overcoming malignant tumors, genetic diseases, infectious diseases and so on. Gene therapy is to introduce a normal gene or a therapeutic gene into a human target cell using biological, physical and chemical methods to correct a gene defect or a functional disorder, thereby treating diseases. How to efficiently and safely transport an exogenous substance from outside to inside of the cell is the key of the gene therapy.

At present, methods for introducing a substance into a cell include a viral gene introduction method, an injection method, a gene gun method, an electroporation method, a sound-induced perforation method and so on. In the sound-induced perforation method, a large number of cells and bubbles are simultaneously added into a solution, the bubbles and cells are well shaken to evenly scatter the bubbles among the cells, and the mixed solution is exposed to an ultrasonic wave, the bubbles generate a cavitation effect under an action of the ultrasonic waves, which causes physical phenomena, such as expansion, implosion, a micro sound flow, a micro jet flow, a shock wave and etc., and these physical phenomena may form micro pores on a surface of the cell to cause change of permeability of a cell membrane.

Research shows that when ultrasonic contrast bubbles are added into a cell solution, the radial vibration of the bubbles under an action of an ultrasonic wave, causes a steady or transient cavitation effect, which may significantly improve the opening efficiency of the cell membrane. In case of transient cavitation of a bubble near a cell, a micro riptide, an acoustic micro flow and a shock wave formed by asymmetric breaking of the bubble are important physical mechanisms for causing an acoustic through hole. The integrity of the cell membrane and the activity of the cell are directly determined by a shear stress corresponding to the micro riptide. When a distance between the bubble and the cell is too large, the shear stress corresponding to a micro jet flow is not enough to damage the integrity of the cell membrane structure, and the opening efficiency of the cell is low; and when the distance between the bubble and the cell is too small, although the opening efficiency of the cell may be obviously improved, a too large shear stress may cause an adherent cell separating from a substrate, and a lethal damage is formed on a surface of the cell membrane.

Therefore, in order to achieve good opening efficiency and perforation effect of the cell, it is necessary to control the distance between the bubble and the cell within a certain distance range. However, the device for acoustic perforation in the related art cannot precisely control the distance between the cell and the bubble, thereby making the shear stress applied to the cell unstable.

SUMMARY

In view of this, the embodiments of the present disclosure aim to provide a microfluidic apparatus, and a system and method for introducing a substance into a cell.

In a first aspect, the embodiments of the present disclosure provide a microfluidic apparatus, which includes a cavity channel, a bulk wave generating device and a surface acoustic wave generating device;

a microstructure is arranged on an inner wall of the cavity channel, and the microstructure is constructed for forming a bubble by a solution at the microstructure when the solution is injected into the cavity channel;

the bulk wave generating device is configured to generate a bulk wave, so that the bulk wave enables the bubble to resonate for generating a flow field;

the surface acoustic wave generating device is configured to generate a surface acoustic wave and control a position of at least one particle in the solution.

In an embodiment, at least one of the microstructure is provided; in an embodiment, the microstructure is a concave trap or hole on the inner wall of the cavity channel.

In an embodiment, the surface acoustic wave generating device controls the particle to be arranged in a straight line and controls the position of the particle in the flow field.

In an embodiment, the cavity channel is made of a transparent material; in an embodiment, the cavity channel is a silicone cavity channel; in an embodiment, the cavity channel is a polydimethylsiloxane cavity channel;

in an embodiment, the bulk wave generating device is a bulk wave transducer;

in an embodiment, the surface acoustic wave generating device is an interdigital transducer.

In a second aspect, the embodiments of the present disclosure provide a system for introducing a substance into a cell, where the system includes the microfluidic apparatus according to the first aspect and an injection device;

the injection device is connected to an inlet of the cavity channel of the microfluidic apparatus, the injection device is configured to inject a solution containing the cell into the cavity channel of the microfluidic apparatus, and the bubble is generated by the solution at the microstructure of the cavity channel;

the microfluidic apparatus is configured to:

generate the bulk wave, where the bulk wave enables the bubble to resonate, causes vibration of the solution in the cavity channel, and generates a flow field in the cavity channel, each position in the flow field corresponds to a different shear stress; and control a position of the cell in the flow field relative to the microstructure to enable the cell to flow through a preset position when the cell flows in the flow field, where a reversible through hole is formed on the cell under an action of a shear stress corresponding to the preset position, and the substance in the solution enters the cell through the reversible through hole.

In an embodiment, the system further includes a signal generator and a power amplifier;

the signal generator is configured to generate a sine wave signal and send the sine wave signal to the power amplifier; and the power amplifier is configured to amplify the sine wave signal and send the amplified sine wave signal to the microfluidic apparatus.

In an embodiment, the system further includes a cell recovery container;

the cell recovery container is connected to an outlet of the cavity channel.

In a third aspect, the embodiments of the present disclosure provide a method for introducing a substance into a cell, where the method includes steps described below.

A solution containing the cell is injected into a cavity channel of a microfluidic apparatus, where the solution containing the cell generates a bubble at a microstructure of the cavity channel;

a bulk wave generating device of the microfluidic apparatus generates a bulk wave, where the bulk wave enables the bubble to resonate, causes vibration of the solution in the cavity channel, and generates a first flow field in the cavity channel, each position in the first flow field corresponds to a different shear stress; and a surface acoustic wave generating device of the microfluidic apparatus controls a position of the cell in the first flow field relative to the microstructure for enabling the cell to flow through a preset position when the cell flows in the first flow field, where the cell generates a reversible through hole under an action of a shear stress corresponding to the preset position, and the substance in the solution enters the cell through the reversible through hole.

In an embodiment, a shear stress corresponding to the each position in the first flow field is determined in a following manner:

injecting a solution containing a trace particle into PDMS cavity channel, where the injected solution containing the trace particle generates an arc-shaped bubble at the microstructure of the cavity channel;

using a bulk wave transducer to enable the bubble to resonate, cause vibration of fluid in the PDMS cavity channel, and generate a second flow field in the PDMS cavity channel;

using a computer to determine a shear stress corresponding to each position in the second flow field according to a flow state of the trace particle in the second flow field; and determining the shear stress corresponding to the each position in the second flow field as the shear stress corresponding to the each position in the first flow field.

In an embodiment, the method further includes steps described below.

A signal generator generates a sine wave signal and sends the sine wave signal to a power amplifier;

the power amplifier amplifies the sine wave signal and sends the amplified sine wave signal to the microfluidic apparatus; and a position of the cell in the first flow field relative to the microstructure is adjusted through adjustment of a phase of the sine wave signal generated by the signal generator.

According to the microfluidic apparatus, the system and method for introducing a substance into a cell provided by the embodiments of the present disclosure, the position of the at least particle in the solution can be accurately controlled through the surface acoustic wave generating device, and further the shearing stress on the particle in the solution can be accurately controlled.

In order to make above purposes, features and advantages of the present disclosure comprehensible, embodiments accompanied with drawings are described in detail below.

BRIEF DESCRIPTION OF DRAWINGS

In order to more clearly describe the present disclosure, drawings needed in the embodiments will be briefly introduced as follows, it should be understood that the following drawings only show some embodiments of the present disclosure and should not be considered as limitation of the protection scope, for those skilled in the art, other relevant drawings may be obtained according to these drawings without creative work.

Figure 1:
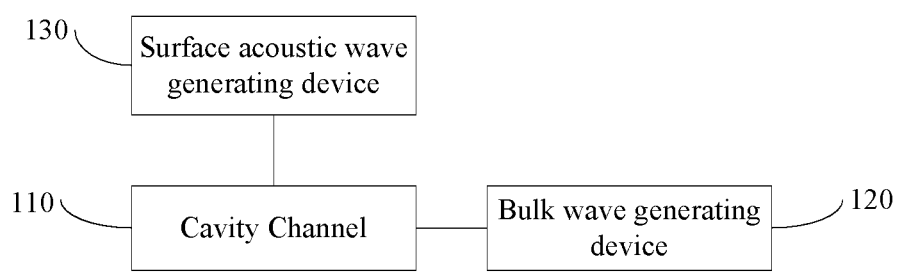
FIG. 1 shows a schematic structural diagram of a microfluidic apparatus according to embodiment 1 of the present disclosure.

Reference signs in FIG. 1:
110: Cavity channel; 120: Bulk wave generating device, 130: Surface acoustic wave generating device;
Reference signs in FIG. 2:
111: Inlet; 112: Microstructure; 113: Outlet;
Reference signs in FIG. 3:
310: Piezoelectric substrate; 320: Interdigital electrode;
Reference signs in FIG. 4:
410: PDMS cavity channel; 420: Bulk wave transducer;
Reference signs in FIG. 5:
510: Injection device; 520: Microfluidic apparatus;
Reference signs in FIG. 6:
610: Micro injection pump; 650: Pipeline; 660: Cell recovery container; 670: Power amplifier; 680: Signal generator.

DETAILED DESCRIPTION

It is considered that when a substance is introduced into a cell by the acoustic perforation method, the apparatus for acoustic perforation in the related art cannot accurately control the distance between the cell and the bubble, thereby making the shearing stress applied to the cell unstable. Based on this, the embodiments of the present disclosure provide a microfluidic apparatus, a system and method for introducing a substance into a cell, which will be described by the embodiments below.

Embodiment 1

The present disclosure relates to a microfluidic apparatus. The apparatus includes a cavity channel and a bulk wave generating device.

A microstructure is arranged on an inner wall of the cavity channel, this microstructure is constructed for forming a bubble by a solution at the microstructure when the solution is injected into the cavity channel; and the bulk wave generating device is configured to generate a bulk wave.

In an embodiment, the microfluidic apparatus further includes a surface acoustic wave generating device, which is configured to generate a surface acoustic wave and control a position of at least one particle in the solution.

The embodiments of the present disclosure provide a microfluidic apparatus. As shown in FIG. 1, the apparatus includes a cavity channel 110, a bulk wave generating device 120 and a surface acoustic wave generating device 130.

A microstructure is arranged on an inner wall of the cavity channel 110. When a solution is injected into the cavity channel 110, the solution forms a bubble at the microstructure.

The bulk wave generating device 120 is configured to generate a bulk wave.

The surface acoustic wave generating device 130 is configured to generate a surface acoustic wave and control a position of at least one particle in the solution.

According to some embodiments, the cavity channel 110 may be made of a transparent material, and the cavity channel 110 may be a silicone cavity channel or a polydimethylsiloxane (PDMS) cavity channel. The bulk wave generating device 120 may be a bulk wave transducer. The surface acoustic wave generating device 130 may be an interdigital transducer.

According to some embodiments, at least one of the microstructure is provided in the cavity channel 110. According to some embodiments, the microstructure is a concave trap or hole on the inner wall of the cavity channel 110.

Figure 2:
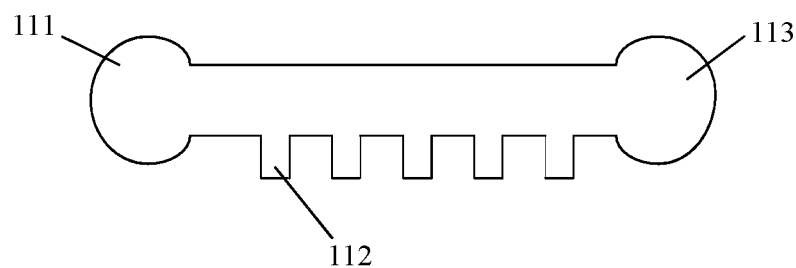
FIG. 2 shows a schematic structural diagram of a cavity channel in a microfluidic apparatus according to embodiment 1 of the present disclosure.

As shown in FIG. 2, a schematic structural diagram of a possible cavity channel 110 is illustrated. When the solution is injected into the cavity channel 110 through an inlet 111 of the cavity channel 110, the solution will not flow into the microstructure 112 of the cavity channel 110, but forms an arc-shaped bubble at the microstructure 112. 113 denotes an outlet of the cavity channel 110, through which a particle in the solution or a part of the solution flows out of the cavity channel 110.

The above FIG. 2 only shows a situation where the cavity channel 110 includes five microstructures 112. However, the embodiments of the present disclosure are not limited thereto. The specific number of microstructures 112 may be set according to a specific application scenario.

In operation, the above-mentioned bulk wave generating device 120 emits a bulk wave outwards, and the frequency of the emitted bulk wave is the resonance frequency of the bubble generated at the microstructure. Therefore, the generated bulk wave enables the bubble to resonate, and the resonance of the bubble drives the solution in the cavity channel 110 to flow, thus generating a flow field is in the cavity channel 110.

The resonance frequency may be determined according to a radius of a circle to which an arc of the arc-shaped bubble belongs, which specifically includes: according to the radius of the circle to which the arc of the arc-shaped bubble belongs, the resonance frequency is determined by a following formula:

$$f^2 = \frac{1}{4\rho\pi^2 a^2}\left\{3\kappa\left(p + \frac{2\sigma}{a}\right) - \frac{2\sigma}{a}\right\}$$

where in the formula, f is the resonance frequency of the bubble, σ is a surface tension of fluid in the flow field, p is a fluid pressure in the flow field, κ is a polytropic index of gas in the bubble, ρ is a density of the fluid in the flow field, a is a radius of the circle to which the arc of the bubble belongs.

The surface acoustic wave generating device 130 controls the particle to be arranged in a straight line and controls the position of the particle in the flow field.

The surface acoustic wave generating device 130 controls the position of the particle in the flow field relative to the microstructure. When the cavity channel is horizontally placed, the surface acoustic wave generating device 130 may control the position of the particle at vertical direction in the flow field.

In an embodiment of the present disclosure, when the cavity channel is horizontally placed, the position of the particle in the flow field relative to the microstructure, i.e., the position at the vertical direction in the flow field, may be further adjusted by adjustment of a phase of an input signal of the surface acoustic wave generating device 130, which is specifically described below.

When two surface acoustic wave generating devices 130 are in operation at the same time, a one-dimensional standing wave field will be formed in the cavity channel 110. In addition, under an action of an ultrasonic radiation force generated by the surface acoustic wave generating device 130, particles in the cavity channel 110 will be arranged at wave nodes of a standing wave. The adjustment of a phase of an input signal of one surface acoustic wave generating device 130 may move up or down the surface acoustic wave generated by this surface acoustic wave generating device 130, and thus cause the wave nodes of the standing wave formed from superposition with a surface acoustic wave generated by the other surface acoustic wave generating device 130 to move up or down. Since the particles are fixed at the positions of the wave nodes, the particles in the cavity channel 110 move up and down as a whole along with up and down movements of the nodes, so that the positions of the particles at the vertical direction in the flow field in the cavity channel may be adjusted.

The distance of the particles moving along the vertical direction and the phase of the input signal of the surface acoustic wave generating device 130 satisfy a following relationship:

$$\Delta x = (n-1)\frac{\lambda}{2} + \frac{\lambda}{720°}\varphi_x, \text{ where } \varphi_x \in [0°, 360°]$$

where in the above formula, Δx is a displacement of the particles, λ is a wavelength of the surface acoustic waves generated by the surface acoustic wave generating devices 130, $\varphi_x$ is a variation of the relative phase between the surface acoustic wave generating devices 130, n is a number of times of adjusting a phase of an input signal of the signal generator from 0° to 360°, where n is equal to 1, 2, 3 . . . .

When the phases of the input signals of the surface acoustic wave generating devices 130 are fixed, the positions of the particles at the vertical direction in the flow field will no longer change. As such, the positions of the particles at the vertical direction of the flow field can be accurately controlled.

Figure 3:
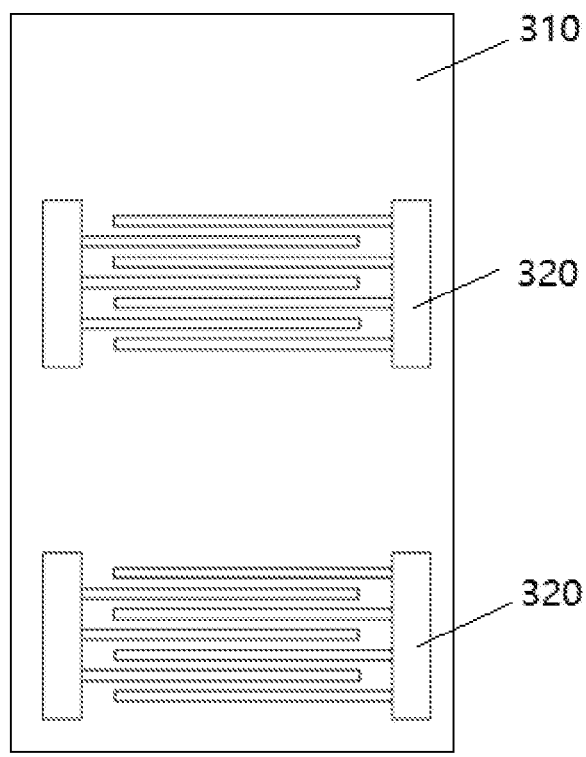
FIG. 3 shows a schematic structural diagram of an interdigital transducer in a microfluidic apparatus according to embodiment 1 of the present disclosure.

The surface acoustic wave generating device 130 described above may include a pair of interdigital transducers, i.e., a pair of interdigital electrodes plated on a piezoelectric substrate, as shown in a structural schematic diagram of FIG. 3. One possible structural schematic diagram of the surface acoustic wave generating device 130 is shown in FIG. 3.

As shown in FIG. 3, the surface acoustic wave generating device 130 includes a piezoelectric substrate 310 and a pair of interdigital electrodes 320. The interdigital transducer is formed by plating the pair of interdigital electrodes 320 on the piezoelectric substrate 310. In order to obtain a relatively large electromechanical coupling coefficient, the interdigital transducer according to the embodiment of the present disclosure may use 128° YX double-sided polished lithium niobate as the piezoelectric substrate.

The interdigital transducer includes a piezoelectric substrate and an interdigital electrode, that is, the interdigital transducer is formed by plating an interdigital electrode on the piezoelectric substrate.

The interdigital transducer may be manufactured through a process flow, which includes gluing, photoetching, coating, stripping and so on.

First, the piezoelectric substrate is coated with glue. The positive photoresist AZ4620 is spin-coated on a surface of the completely cleaned piezoelectric substrate material at 5000 rpm for 30 s. A chip is placed on a heating plate at 120° C. and baked for 3 min. A step profiler is used for test a thickness of the photoresist, and the test result shows that the thickness of the photoresist is about 5 μm.

Then, the glued piezoelectric substrate is exposed and developed. The prepared film is covered on the glued piezoelectric substrate for exposure. A part of the photoresist at a place of the film where light passes through will be solidified. When AZ400 is used for development, the solidified part of the photoresist will not be dissolved while the non-solidified part will be dissolved. After development, the chip is baked on a heating plate at 150° C. for 10 min.

Magnetron sputtering is performed on the baked piezoelectric substrate to grow a metal layer with a thickness of about 200 nm.

The aluminum film substrate with the metal layer is placed in an acetone solution, and the photoresist is stripped by ultrasonic vibration of an ultrasonic cleaning machine to obtain the interdigital transducer.

The cavity channel 110 in an embodiment of the present disclosure may be a PDMS cavity channel, and the PDMS cavity channel is manufactured through a process flow including preprocessing, gluing and pre-drying, exposure and development, PDMS pouring, PDMS stripping, and so on.

The manufacturing process is specifically described below.

First, preprocessing is performed. Residual impurities on the surface of the silicon substrate, such as, dust, organic adsorbate, are removed through acid washing, alcohol washing, water washing and so on, and the cleaned silicon substrate is placed on a clean place to be dried. SU-8(50) negative photoresist is spin-coated by a glue spreader at 3000 rpm for 30 s. The SU-8(50) has a thickness of about 50 μm. After that, a silicon wafer is horizontally placed on a heating plate at 90° C. for 1 hour to volatilize solvent in the photoresist, so that the adhesion between the photoresist and the silicon wafer is enhanced.

The prepared film is placed on the glued silicon wafer. The photoresist is exposed by an exposure machine with an exposure dose of 600 CJ/cm$^2$ for 30 s. The exposed silicon wafer is soaked with a developer. The photoresist in an unexposed area is dissolved, and the photoresist in an exposed area remains. After development, the silicon wafer is baked on a heating plate at 150° C. and is baked for 10 min;

Glue A and glue B of the PDMS are well mixed at a mass ratio of 10:1, and poured into a culture dish where the silicon wafer is located. The culture dish is vacuumized to remove bubbles form the PDMS. Finally the culture dish is placed in an oven at 80° C. for 30 min to solidify the PDMS.

The PDMS containing the cavity channel and microstructure is cut off and completely peeled off from the silicon wafer. At last the micro cavity channel is perforated with a hole puncher to form an inlet and an outlet.

Plasma processing is performed on the ready-made interdigital transducer and PDMS cavity channel with a power of 150 W for 70 s. Then the PDMS cavity channel is stuck downwards between the two interdigital electrodes of the interdigital transducer and baked at 80° C. for 20 min.

Figure 4:
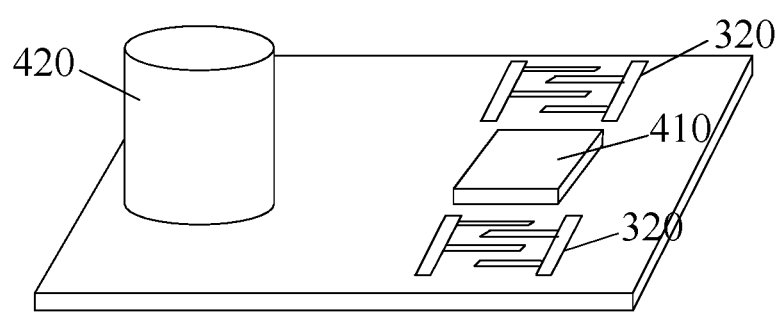
FIG. 4 shows a specific structural diagram of a microfluidic apparatus according to embodiment 1 of the present disclosure.

FIG. 4 shows a possible specific structural diagram of a microfluidic apparatus according to an embodiment of the present disclosure. The microfluidic apparatus includes a PDMS cavity channel 410, a bulk wave transducer 420 and an interdigital transducer. The interdigital transducer is provided with two interdigital electrodes 320. The PDMS cavity channel 410, the bulk wave transducer 420 and the interdigital transducer may be integrated on a same chip.

A solution is injected into the PDMS cavity channel 410. An arc-shaped bubble is generated at a microstructure of the PDMS cavity channel 410 when the solution is injected into the PDMS cavity channel 410. In operation, the bulk wave transducer 420 emits a bulk wave outwards. The frequency of the emitted bulk wave is consistent with the resonant frequency of the bubble in the PDMS cavity channel 410. Therefore, the bulk wave generated by the bulk wave transducer 420 causes vibration of the bubble in the PDMS cavity channel 410, so that the vibration of the bubble drives the solution in the PDMS cavity channel 410 to vibrate, so as to generate a flow field.

In addition, the PDMS cavity channel 410 is located in the middle of the two interdigital electrodes 320 of the interdigital transducer. In operation, each of the two interdigital electrodes 320 emits a surface acoustic wave signal outwards. The emitted surface acoustic waves control a position of at least one particle in the flow field relative to the microstructure.

The embodiment of the present disclosure provides a microfluidic apparatus, which can accurately control the position of the particle in the solution through the surface acoustic wave generating device, so as to accurately control the shear stress of the particle in the solution.

Embodiment 2

Figure 5:
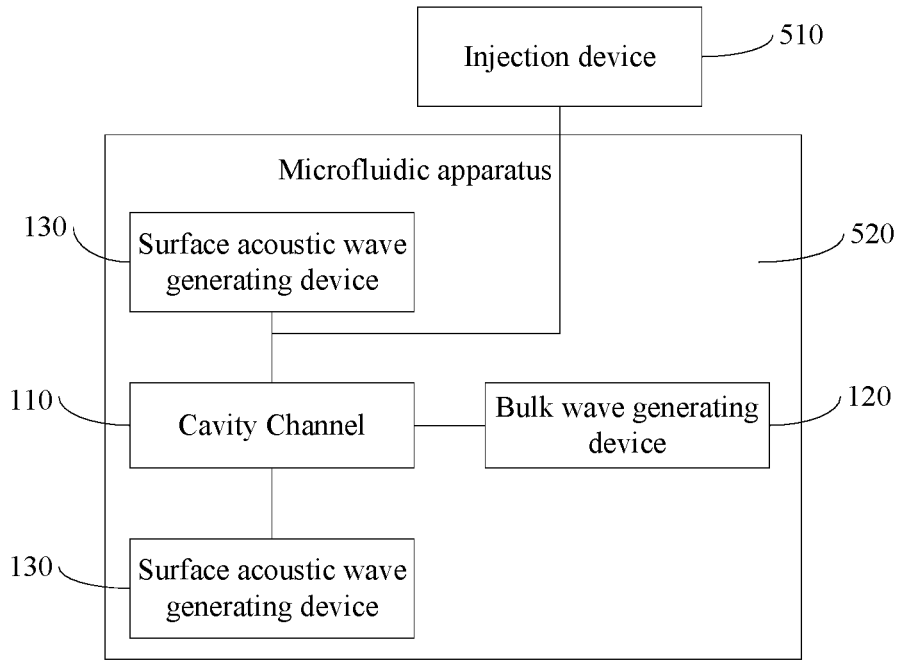
FIG. 5 shows a schematic structural diagram of a system for introducing a substance into a cell according to embodiment 2 of the present disclosure.

The embodiment of the present disclosure provides a system for introducing a substance into a cell. As shown in FIG. 5, the system includes an injection device and the microfluidic apparatus 520 according to the embodiment 1.

The injection device 510 is used to inject a solution containing the cell into the cavity channel of the microfluidic apparatus 520, where a bubble is generated by the solution at the microstructure of the cavity channel;

the microfluidic apparatus 520 is configured to generate the bulk wave, where the bulk wave enables the bubble to resonate, which causes vibration of the solution in the cavity channel and generates a flow field in the cavity channel, each position in the flow field corresponds to a different shear stress; and the microfluidic apparatus 520 is configured to control a position of the cell in the flow field relative to the microstructure, so to enable the cell to flow through a preset position when the cell flows in the flow field, where a reversible through hole is formed on the cell under an action of a shear stress corresponding to the preset position, and the substance in the solution enters the cell through the reversible through hole.

According to some embodiments, the above substance may be a gene fragment, a drug molecule and so on.

The injection device 510 is connected to the cavity channel of the microfluidic apparatus 520 through a pipeline, and the injection device 510 may be a micro injection pump.

According to some embodiments, the system further includes a signal generator and a power amplifier;

the signal generator is configured to generate a sine wave signal and send the sine wave signal to the power amplifier;

the power amplifier is configured to amplify the sine wave signal and send the amplified sine wave signal to the microfluidic apparatus.

The system according to the embodiments of the present disclosure may include one signal generator, two multiple signal generators or multiple signal generators. The embodiments of the present disclosure do not limit the number of signal generators as long as a sufficient number of signals may be obtained.

According to some embodiments, the system further includes a cell recovery container;

the cell recovery container is connected to the cavity channel of the microfluidic apparatus 520 through a pipeline, and is used to contain the cell with the introduced substance.

Figure 6:
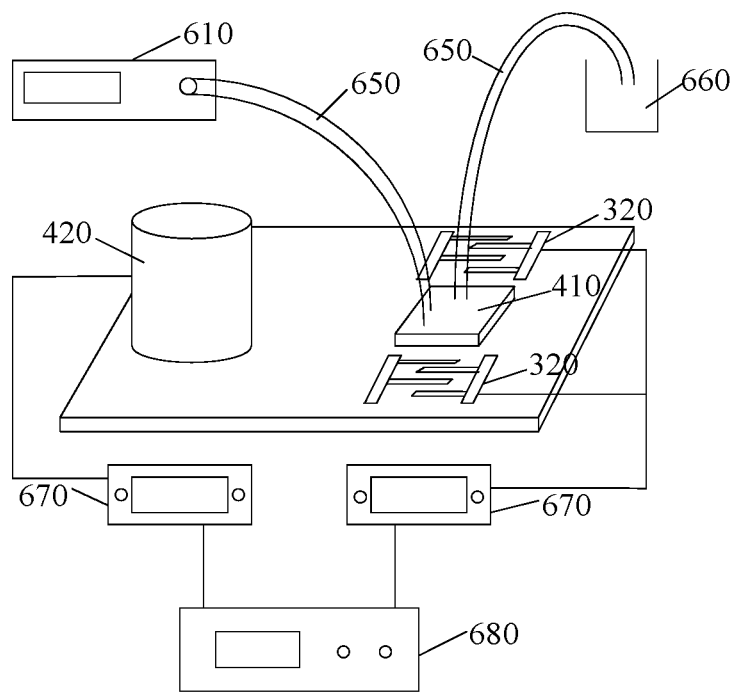
FIG. 6 shows a second structural diagram of a system for introducing a substance into a cell according to embodiment 2 of the present disclosure.

FIG. 6 shows a specific structural diagram of a possible system for introducing a substance into a cell. The system includes a micro injection pump 610, a PDMS cavity channel 410, a bulk wave transducer 420, and a surface acoustic wave generating device. The surface acoustic wave generating device is provided with a pair of interdigital electrodes 320, a pipeline 650, a cell recovery container 660, two power amplifiers 670 and a signal generator 680.

The above-mentioned FIG. 6 only shows one signal generator 680. More than one signal generator may be provided. The specific number of signal generators 680 may be set according to a specific application scenario, and the specific number of signal generators 680 is not limited in the FIG. 6.

In FIG. 6, the micro injection pump 610 is connected to the PDMS cavity channel 410 through the pipeline 650, and a solution containing a cell is injected into the PDMS cavity channel 410 through the pipeline 650. After the solution is injected into the PDMS cavity channel 410, an arc-shaped bubble is generated at the microstructure of the PDMS cavity channel 410. The bulk wave transducer 420 is connected to the power amplifier 670, and the power amplifier 670 is connected to the signal generator 680. The signal generator 680 outputs a sine wave signal and sends the output sine wave signal to the power amplifier 670. The power amplifier 670 amplifies the signal and sends the amplified signal to the bulk wave transducer 420, so as to drive the bulk wave transducer 420 to operate. The bulk wave transducer 420 emits a bulk wave outwards. The frequency of the generated bulk wave is consistent with the resonant frequency of the bubble in the PDMS cavity channel 410. Therefore, the bulk wave generated by the bulk wave transducer 420 causes vibration of the bubble in the PDMS cavity channel 410, and the vibration of the bubble drives vibration of fluid in the PDMS cavity 410 to generate a flow field.

In addition, the PDMS cavity channel 410 is located between the two interdigital electrodes 320. Each of the interdigital electrodes 320 is connected to the power amplifier 670. The power amplifier 670 is connected to the signal generator 680. The signal generator 680 outputs a sine wave signal and sends the output sine wave signal to the power amplifier 670. The power amplifier 670 amplifies the signal and sends the amplified signal to the interdigital electrodes 320, so as to drive the interdigital electrode 320 to operate. When the interdigital electrodes 320 are in operation, a surface acoustic wave signal is emitted outwards, and the emitted surface acoustic wave controls a position of the cell in the flow field relative to the microstructure. In this way, when the cell flows in the horizontal direction, each cell may pass through a preset position; and when the each cell flows through the preset position, a reversible through hole is generated under an action of a shear stress at the preset position, and a substance in the solution enters the cell through the reversible through hole.

According to the system for introducing a substance into a cell provided by the embodiment of the present disclosure, the microfluidic apparatus can accurately control the position of the cell in the flow field, so that the each cell passes through the preset position when the each cell flows in the flow field, and further accurately control the shear stress applied to the each cell.

Embodiment 3

The embodiment of the present disclosure provides a method for introducing a substance into a cell. The method is applied to the system for introducing a substance into a cell in the above embodiment 2. The method can accurately control the position of the cell in the flow field relative to the microstructure through the bulk wave generating device of the microfluidic apparatus, so that each cell passes through a preset position when the cell flows in the flow field, and further accurately control the shear stress applied to the cell.

In the present embodiment of the present disclosure, the substance, which is introduced into the cell, may be a gene fragment, a drug molecule, etc., and a user may put the substance, which needs to be introduced into the cell, into the solution according to an actual requirement. Then the substance is introduced into the cell by the method according to the embodiment of the present disclosure.

Figure 7:
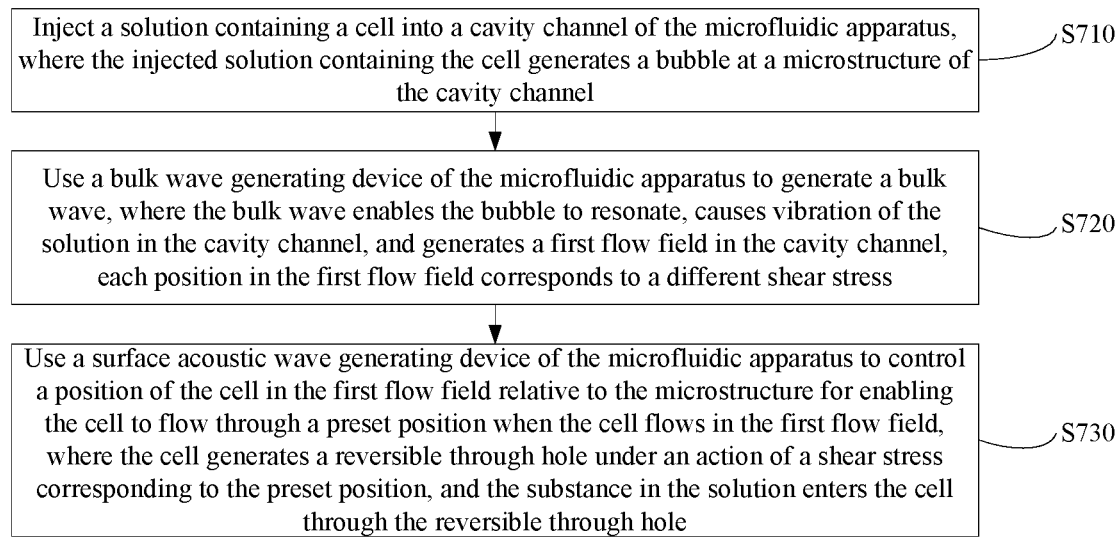
FIG. 7 shows a flowchart of a method for introducing a substance into a cell according to embodiment 3 of the present disclosure.

The method provided by the embodiment of the present disclosure is used to introduce a substance into a cell. As shown in FIG. 7, the method includes steps S710 to S730, which are specifically described as follows.

In S710, a solution containing a cell is injected into a cavity channel of the microfluidic apparatus, where the solution containing the cell generates a bubble at a microstructure of the cavity channel.

According to some embodiments, the cavity channel includes at least one microstructure, and the solution generates an arc-shaped bubble at each microstructure.

The above-mentioned solution containing the cell is injected into the cavity channel of the microfluidic apparatus through an injection device, which may be a micro injection pump.

In some embodiments, the solution containing the cell may be continuously injected into the cavity channel of the microfluidic apparatus.

In S720, a bulk wave generating device of the microfluidic apparatus is used to generate a bulk wave, where the bulk wave enables the bubble to resonate, causes vibration of the solution in the cavity channel, and generates a first flow field in the cavity channel, each position in the first flow field corresponds to a different shear stress.

Each position in the first flow field corresponds to a different shear stress, where the shear stress in each position may be determined in following manners.

Before the substance is introduced into the cell using the method according to the embodiments of the present disclosure, i.e., before the solution containing the cell is injected into the cavity channel, the shear stress corresponding to each position in the first flow field generated by the solution in the cavity channel is determined.

In an embodiment of the present disclosure, the shear stress corresponding to each position in the flow field may be determined by adding a trace particle into the flow field and through flow of the trace particle in the flow field.

The method includes steps described below. A solution containing a trace particle is injected into the cavity channel, where the injected solution containing the trace particle generates an arc-shaped bubble at the microstructure of the cavity channel; a bulk wave transducer is used to enable the bubble to resonate, cause vibration of fluid in the cavity channel, and generate a second flow field in the cavity channel; a computer is used to determine a shear stress corresponding to each position in the second flow field according to a flow state of the trace particle in the second flow field; and the shear stress corresponding to each position in the second flow field is determined as the shear stress corresponding to each position in the first flow field.

The second flow field generated by the solution containing the trace particle in the cavity channel is as same as the first flow field generated by the solution containing the cell in the cavity channel, these two flow fields are both caused by the bulk wave generated using a same bulk wave generating device. Therefore, the shear stress corresponding to each position in the second flow field may be determined as the shear stress corresponding to each position in the first flow field.

According to a flow state of the trace particle in the second flow field, the corresponding shear stress corresponding to each position in the second flow field is determined by a computer. This step includes steps described below.

Through continuously shooting the flow state of the trace particle in the second flow field by a high-speed camera, a state image of the trace particle is obtained; according to the above state image, a fluid velocity of the trace particle corresponding to each position in the second flow field is determined by a computer; and the shear stress corresponding to each position is determined by a computer according to a fluid velocity of the tracer particle corresponding to each position.

In an embodiment of the present disclosure, the high-speed camera continuously shoots multiple frames of flow state images of the trace particle in the second flow field. Any two frames of the state image are taken out from the multiple frames of the state image. The two frames of the state image are divided into same multiple small windows in a same manner, and cross-correlation calculation is performed on corresponding window for two sequential frames. Specifically, a cross-correlation value of the corresponding window for the two frames may be calculated according to a following formula;

$$R(m, n) = \frac{\sum_{i=1}^{M}\sum_{j=1}^{N}(f(i, j) - \mu_f)(g(i+m, j+n) - \mu_g)}{\sqrt{\sum_{i=1}^{M}\sum_{j=1}^{N}(f(i, j) - \mu_f)^2 \sum_{i=1}^{M}\sum_{j=1}^{N}(g(i+m, j+n) - \mu_g)^2}}$$

in the above formula, R(m, n) is a cross-correlation value of the corresponding window for the two sequential frames, M*N is a size of the above window, where M and N may be represented in pixels, m and n may also be represented in pixels, f(i, j) is a pixel value at a location of (i, j) in the former frame, g(i+m, j+n) is a pixel value at a location of (i+m, j+n) in the later frame, $\mu_f$ is an average value of a pixel of f(i, j) corresponding to all pixels within the window of the former frame, $\mu_g$ is an average value of a pixel of g(i+m, j+n) corresponding to all pixels within the window of the later frame, where m and n are fixed for each R(m, n), each R(m, n) needs to be calculated.

The calculated cross-correlation value of the corresponding window for the two frames is determined as a displacement of the windows, a size of the divided small windows is gradually reduced, a calculated spatial resolution is increased, a displacement of each position in the second flow field is calculated by the above method. The displacement is divided by a time interval between the two sequential frames to obtain a fluid velocity of the trace particle at each position.

After the fluid velocity of the trace particle at each position in the second flow field is determined, the shear stress corresponding to each position is determined according to the fluid velocity of the trace particle at each position using a following formula:

$$WSS = \rho\mu\left(\left(\frac{dV_y}{dx}\right)^2 + \left(\frac{dV_x}{dy}\right)^2\right)^{\frac{1}{2}}$$

in the above formula, ρ represents a density of fluid in the second flow field, μ is a viscosity of the fluid in the second flow field, $V_x$ is a fluid velocity of the fluid in the horizontal direction in the second flow field, $V_y$ is a fluid velocity in the vertical direction in the second flow field, and WSS is a shear stress corresponding to the above position.

The velocity of the trace particle at a certain position in the second flow field is a velocity of the fluid at that position. Therefore, the velocity of the flow field at each position may be known by the velocity of the trace particle at each position.

In an embodiment of the present disclosure, a shear stress corresponding to the certain position is determined according to a velocity of the fluid at a certain position and around the certain position in the flow field. For example, the shear stress corresponding to position A in the flow field is determined by the velocity of the fluid at the position A and around the position A in the flow field.

In S730, a surface acoustic wave generating device of the microfluidic apparatus is used to control a position of the cell in the first flow field relative to the microstructure, which enables the cell to flow through a preset position when the cell flows in the first flow field, where the cell generates a reversible through hole under an action of a shear stress corresponding to the preset position, and the substance in the solution enters the cell through the reversible through hole.

The surface acoustic wave generating device generates a surface acoustic wave signal when the surface acoustic wave generating device is in operation. The surface acoustic wave signal controls the cell in the cavity channel to be arranged in a straight line, and controls the position of the cell in the first flow field relative to the microstructure, so that a distance between the bubble and the cell in the microstructure of the cavity channel is fixed. In this way when the cell moves in the horizontal direction in the first flow field, each cell flows through the preset position, a reversible through hole is generated by a shear stress at the preset position, which enables a substance in the solution to enter the cell through the reversible through hole.

The cells in the cavity channel are arranged in a single row in a manner of setting a width of the cavity channel. Therefore, in an embodiment of the present disclosure, the cavity channel has a width greater than a width of the cells and less than half of a wavelength of a surface acoustic wave generated by the surface acoustic wave generating device, so that only one row of cells may pass through the cavity channel.

The preset position may be adjusted and determined as follows.

In an embodiment of the present disclosure, a signal generator generates a sine wave signal and sends the sine wave signal to a power amplifier; the power amplifier amplifies the sine wave signal and sends the amplified sine wave signal to a bulk wave transducer and an interdigital transducer; a position of the cell in the first flow field relative to the microstructure is adjusted through adjustment of a phase of the sine wave signal generated by the signal generator.

The signal generator may generate three sine wave signals: one is amplified by a first power amplifier and sent to the bulk wave generating device; and the other two sine wave signals are amplified by a second power amplifier and sent to a pair of interdigital electrodes of the surface acoustic wave generating device.

Alternatively, three signal generators are provided: one is used for generating a sine wave signal required by the bulk wave generating device; and the other two are used for generating sine wave signals required by the surface acoustic wave generating device.

In an embodiment of the present disclosure, the specific number of signal generators is not set; and in a specific application scenario, the number may be selected according to an actual application.

In an embodiment of the present disclosure, the position of the cell in the first flow field relative to the microstructure may be adjusted through adjustment of a phase of the sine wave signal generated by the signal generator.

The surface acoustic wave generating device is an interdigital transducer.

In an embodiment of the present disclosure, the cavity channel is arranged between the two interdigital electrodes of the interdigital transducer, so that the cavity channel may simultaneously receive surface acoustic wave signals emitted by the two interdigital electrodes.

The specific process for the user to adjust the positions of the cells in the first flow field through the adjustment of the signal generator includes: when the interdigital transducer is in operation, a one-dimensional standing wave field will be formed in the cavity channel; under an action of a ultrasonic radiation force generated by the interdigital transducer, cells in the cavity channel will be arranged at wave nodes of the standing wave; through adjustment of a frequency of an input signal of one surface acoustic wave generating device, a surface acoustic wave generated by the surface acoustic wave generating device will move up or down, which causes the wave nodes of the standing wave to superpose with the surface acoustic wave generated by the other surface acoustic wave generating device to move up or down. Since the cells are fixed at the positions of the wave nodes, the cells in the cavity channel move up and down as a whole along with up and down movements of the nodes, so that the positions of the cells in the first flow field of the cavity channel relative to the microstructure may be adjusted.

The distance of movement of the cells and the phase of the sine wave signal output by the signal generator satisfy following relationships:

$$\Delta x = (n-1)\frac{\lambda}{2} + \frac{\lambda}{720°}\varphi_x, \text{ where } \phi_x \in [0°, 360°]$$

in the above formula, $\Delta x$ is a displacement of the particles, $\lambda$ is a wavelength of the surface acoustic waves generated by the interdigital transducer, $\varphi_x$ is a variation of the relative phase of the interdigital transducer, n is a number of times of adjusting a phase of an input signal of the signal generator from 0° to 360°, where n is equal to 1, 2, 3 . . . .

When the phases of the output signals of the signal generator are fixed, the position of the cell in the first flow field relative to the microstructure will not change.

In an adjustment process, in order to make the cell flow through the preset position when it flows in the first flow field, vitality and perforation degree of the cell may be observed by a scanning electron microscope in the process of adjusting the phase of the sine wave signals output by the signal generator.

In order to observe the vitality and perforation degree of the cell, a FDA fluorescent probe and PI fluorescent probe may be added into the solution containing the cell. When the method provided by the embodiments of the present disclosure is used to introduce a substance into a cell, the FDA fluorescent probe and PI fluorescent probe may be added into the solution at the beginning of the process of adjusting the phase of the sine wave signal output by the signal generator. Once the adjustment is completed, it is not necessary to add the FDA fluorescent probe and PI fluorescent probe to the solution. Of course, a user may add the FDA fluorescent probe and PI fluorescent probe to the solution at a time interval during the process of introducing a substance into a cell to observe the vitality and perforation degree of the current cell.

The FDA is a hydrophobic compound, which may penetrate whole cell membrane and enter the cell. Hydrolyze diacetate groups generate a fluorescent product with a high intensity through catalysis of cell lactonase. If the cell membrane is complete, FDA fluorescent molecules will accumulate in the cell and emits green fluorescence. Therefore, the FDA may be used as a label of cell viability.

When the cell produces a reversible through hole under an action of a shear stress, PI will enter a nucleus through the through hole on the surface of the cell membrane and combine with a DNA to generate red fluorescence, and intensity of the red fluorescence may directly reflect a perforation degree of the cell. Therefore, the activity and perforation degree of the cell may be detected by labeling the above two fluorescent probes on the cell.

Therefore, in the process of adjusting the phase of the sine wave signal output by the signal generator, the intensity of the fluorescence in the cell is observed through a scanning electron microscope, the vitality and opening efficiency of the cell at each position of the cell in the first flow field relative to the microstructure are determined according to the intensity of the fluorescence, a position of the cell in the first flow field relative to the microstructure is found. When the vitality and opening efficiency of the cell are determined to be optimal, the phase of the signal output by the signal generator is no longer adjusted, and the signal generator sends a sine wave signal at current phase to the interdigital transducer, so that the relative position of the cell in the first flow field does not change any more. At the same time, when the cell flows in the first flow field, each cell flows through a preset position, and the shear stress at the preset position is an optimal shear stress, thus a reversible through hole is generated, and the substance in the solution enters the cell through the reversible through hole.

When the substance in the solution enters the cell through the reversible through hole, the process of introducing the substance into the cell is completed, and the cell containing the introduced substance is transported to the cell recovery container through a pipeline.

The method for introducing the substance into the cell provided by the embodiment of the present disclosure can accurately control the position of the cell in the flow field relative to the microstructure, so that the each cell passes through a preset position when the cell flows in the flow field, and further accurately control the shear stress applied to the cell.

It should be noted that similar reference signs and letters indicate similar items in the following drawings. Therefore, once an item is defined in one drawing, it does not need to be further defined and explained in the following drawings. In addition, terms of "first", "second", "third" and so on are only used for distinguishing description and may not be understood as indicating or implying relative importance.

What is claimed is:

1. A system for introducing a substance into a cell, comprising:
   the microfluidic apparatus comprising a cavity channel, a bulk wave generating device and a surface acoustic wave generating device;
   wherein a microstructure is arranged on an inner wall of the cavity channel, and the microstructure is constructed for forming a bubble by a solution at the microstructure in a case where the solution is injected into the cavity channel;
   the bulk wave generating device is configured to generate a bulk wave, wherein the bulk wave enables the bubble to resonate for generating a flow field; and
   the surface acoustic wave generating device is configured to generate a surface acoustic wave and control a position of at least one particle in the solution; and
   an injection device, which is connected to an inlet of the cavity channel of the microfluidic apparatus, wherein the injection device is configured to inject a solution containing the cell into the cavity channel of the microfluidic apparatus, and the bubble is generated by the solution at the microstructure of the cavity channel;
   wherein the microfluidic apparatus is configured to:
   generate the bulk wave, wherein the bulk wave enables the bubble to resonate, causes vibration of the solution in the cavity channel, and generates a flow field in the cavity channel, wherein each position in the flow field corresponds to a different shear stress; and
   control a position of the cell in the flow field relative to the microstructure to enable the cell to flow through a preset position in a case where the cell flows in the flow field, wherein a reversible through hole is formed on the cell under an action of a shear stress corresponding to the preset position, and the substance in the solution enters the cell through the reversible through hole.

2. The system according to claim 1, wherein the system further comprises a signal generator and a power amplifier;
   wherein the signal generator is configured to generate a sine wave signal and send the sine wave signal to the power amplifier; and
   the power amplifier is configured to amplify the sine wave signal and send the amplified sine wave signal to the microfluidic apparatus.

3. The system according to claim 1, wherein the system further comprises a cell recovery container;
   wherein the cell recovery container is connected to an outlet of the cavity channel.

4. A method of introducing a substance into a cell, applied to a system for introducing a substance into a cell, comprising:
   the microfluidic apparatus comprising a cavity channel, a bulk wave generating device and a surface acoustic wave generating device;
   wherein a microstructure is arranged on an inner wall of the cavity channel, and the microstructure is constructed for forming a bubble by a solution at the microstructure in a case where the solution is injected into the cavity channel;
   the bulk wave generating device is configured to generate a bulk wave, wherein the bulk wave enables the bubble to resonate for generating a flow field; and
   the surface acoustic wave generating device is configured to generate a surface acoustic wave and control a position of at least one particle in the solution; and
   an injection device, which is connected to an inlet of the cavity channel of the microfluidic apparatus, wherein the injection device is configured to inject a solution containing the cell into the cavity channel of the microfluidic apparatus, and the bubble is generated by the solution at the microstructure of the cavity channel;
   wherein the microfluidic apparatus is configured to:
   generate the bulk wave, wherein the bulk wave enables the bubble to resonate, causes vibration of the solution in the cavity channel, and generates a flow field in the cavity channel, wherein each position in the flow field corresponds to a different shear stress; and
   control a position of the cell in the flow field relative to the microstructure to enable the cell to flow through a preset position in a case where the cell flows in the flow field, wherein a reversible through hole is formed on the cell under an action of a shear stress corresponding to the preset position, and the substance in the solution enters the cell through the reversible through hole, the method comprising the steps of:
   injecting a solution containing the cell into a cavity channel of a microfluidic apparatus, wherein the solution containing the cell generates a bubble at a microstructure of the cavity channel;
   using a bulk wave generating device of the microfluidic apparatus to generate a bulk wave, wherein the bulk wave enables the bubbles to resonate, causes vibration of the solution in the cavity channel, and generates a first flow field in the cavity channel, wherein each position in the first flow field corresponds to a different shear stress; and
   using a surface acoustic wave generating device of the microfluidic apparatus to control a position of the cell in the first flow field relative to the microstructure for enabling the cell to flow through a preset position in a case where the cell flows in the first flow field, wherein the cell generates a reversible through hole under an action of a shear stress corresponding to the preset position, and the substance in the solution enters the cell through the reversible through hole.

5. The method according to claim 4, wherein a shear stress corresponding to the each position in the first flow field is determined in a following manner:

injecting a solution containing a trace particle into the cavity channel, wherein the injected solution containing the trace particle generates an arc-shaped bubble at the microstructure of the cavity channel;

using a bulk wave transducer to enable the bubble to resonate, cause vibration of fluid in the cavity channel, and generate a second flow field in the cavity channel;

using a computer to determine a shear stress corresponding to each position in the second flow field according to a flow state of the trace particle in the second flow field; and determining the shear stress corresponding to the each position in the second flow field as the shear stress corresponding to the each position in the first flow field.

6. The method according to claim 4, wherein the method further comprises:

using a signal generator to generate a sine wave signal and send the sine wave signal to a power amplifier;

using the power amplifier to amplify the sine wave signal and send the amplified sine wave signal to the microfluidic apparatus; and adjusting a position of the cell in the first flow field relative to the microstructure through adjustment of a phase of the sine wave signal generated by the signal generator.

* * * * *